(12) United States Patent  (10) Patent No.: US 9,145,439 B2
Grassi et al.  (45) Date of Patent: Sep. 29, 2015

(54) PROCESS FOR THE PREPARATION OF 6-ALPHA-FLUORO PREGNANES

(71) Applicant: TRIFARMA S.p.A., Milan (IT)

(72) Inventors: Simona Grassi, Saronno (IT); Stefano Mascheroni, Rozzano (IT); Roberto Giani, Locate di Triulzi (IT)

(73) Assignee: TRIFARMA S.P.A., Milan (IT)

( * ) Notice: Subject to any disclaimer, the term of this patent is extended or adjusted under 35 U.S.C. 154(b) by 98 days.

(21) Appl. No.: 14/109,552

(22) Filed: Dec. 17, 2013

(65) Prior Publication Data

US 2014/0179914 A1  Jun. 26, 2014

(30) Foreign Application Priority Data

Dec. 20, 2012  (IT) .......................... MI2012A002200

(51) Int. Cl.
*C07J 71/00* (2006.01)
(52) U.S. Cl.
CPC .................................. *C07J 71/0015* (2013.01)
(58) Field of Classification Search
CPC .................................................... C07J 71/0015
USPC ........................................................... 540/88
See application file for complete search history.

(56) References Cited

U.S. PATENT DOCUMENTS 6,528,666 B1  3/2003  Villax et al.
7,718,793 B2  5/2010  Chernyak et al.

FOREIGN PATENT DOCUMENTS

EP  1 207 166 A2  5/2002
WO  WO 2004/052911 A1  6/2004

*Primary Examiner* — Brenda Coleman
(74) *Attorney, Agent, or Firm* — Arent Fox LLP

(57) ABSTRACT

Disclosed is a process for the preparation of 6-α-fluoro pregnanes of formula I

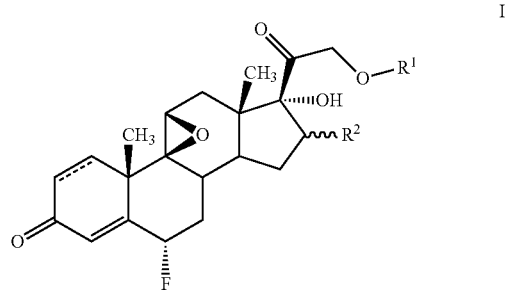

wherein $R^1$ is an acyl group, $R^2$ can be H, alpha methyl or beta methyl, and the dotted line can represent a double bond, comprising fluorination with electrophilic fluorinating agents in the 6 position of compounds of formula III,

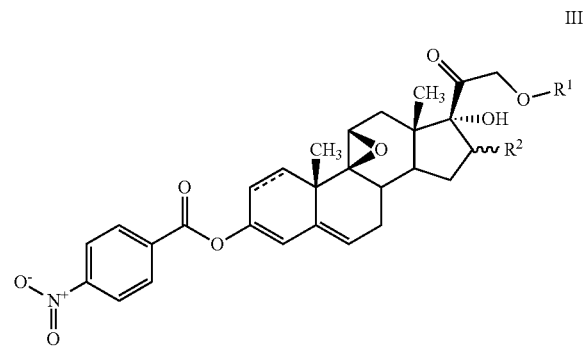

wherein $R^1$, $R^2$ and the dotted line have the meanings stated above, in an inert solvent, in the presence of a basic catalyst at temperatures ranging between 0 and 30° C.

9 Claims, No Drawings

PROCESS FOR THE PREPARATION OF 6-ALPHA-FLUORO PREGNANES

The present invention relates to a process for the preparation of 6-α-fluoro pregnanes.

PRIOR ART

The 6-α-fluoro pregnanes of formula I are used as raw materials for the production of many steroidal active ingredients, such as diflorasone diacetate, difluprednate, flumethasone and derivatives thereof lialobetasol propionate, fluocinonide, fluocinolone acetonide, flunisolide and others.

It is known that fluorination in the 6 position of steroidal structures is not very selective, and as the stereoisomers have different pharmacological properties, it is necessary to obtain the desired isomer (nearly always the 6α isomer) in almost pure form, namely with a 6β isomer content of less than 0.15%.

Over the years, many processes have been developed for Obtaining 6α-fluoro derivatives, all of which present problems of selectivity and overall purity; repeated purifications are therefore required, leading to lower yields and increased costs.

There is consequently a need for highly selective processes, which produce high yields and high quality for industrially viable production.

EP 1207166 and U.S. Pat. No. 7,718,793 claim a process for the production of 6-α-fluoro pregnanes as shown in scheme 1:

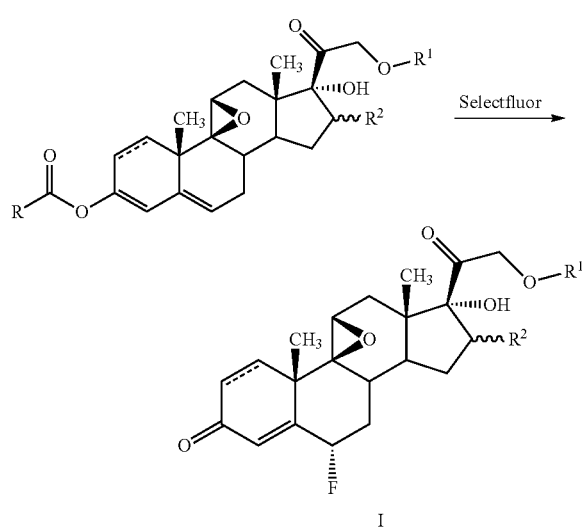

wherein R is an alkyl group, R¹ is an acyl group, R² can be H, OH, alpha methyl or beta methyl, and the dotted line can represent a double bond. Fluorination is conducted with an electrophilic fluorinating agent such as Selectfluor or Accufluor.

However, said process provides a mixture of 6α☐/6β in the ratio of about 95: 5, with significant presence of other impurities such as 4-fluoro, 6--hydroxy, 6 keto derivatives and others.

Repeated purifications of said mixture to obtain a 6α-fluoro of acceptable quality lead to dramatically low yields, and consequently very high costs.

U.S. Pat. No. 6,528,666 describes a process for the production of flumethasone including fluorination in the 6 position of 9β,11-epoxy-16α-methyl-3,17,21-trihydroxy-1,3,5-triene-20-one-21-acetate-3-benzoate with an electrophilic fluorinating agent in a partly aqueous environment.

The mixture obtained, after crystallisation from methanol, has an HPLC purity of about 90%. Once again, the impurities present are those already cited above, and the repeated purifications needed to obtain acceptable quality lead to very low yields and very high costs.

WO 2004/052911 discloses a process of fluorination in the 6 position of compounds of formula II,

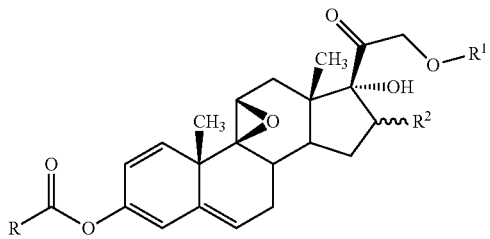

wherein R is phenyl, optionally substituted with chloro, fluoro, hydroxy, methoxy, ethoxy, methoxycarbonyl, methyl, ethyl and dimethylamino, R¹ is an acyl group and R² can be H, OH, alpha methyl or beta methyl, with an electrophilic fluorinating agent and in the presence of large quantities of pyridine methanesulphonate.

All the examples illustrated involve non-isolation of the 3-benzoate of formula II.

In one case only (Example A1) it is reported that the 3-benzoate can be isolated as a crude solid by crushing with diisopropyl ether. We have established that this crushing only makes the mass solid, but has no purification capacity.

It is evident that non-isolation or crushing with diisopropyl ether of the 3-benzoates of formula II leads to fluorinated products also containing impurities deriving from the formation reaction of 3-enolbenzoates. In fact, as also stated in U.S. Pat. No. 6,528,666, the corresponding 6α-fluoro derivatives have a purity of about 90%.

In addition, the use of pyridine methanesulphonate involves the risk of formation of methanesulphonic esters, which are highly carcinogenic substances.

The world health authorities require the almost total absence of said substances to be demonstrated.

DESCRIPTION OF THE INVENTION

It has now been found that the 3-(4-nitrobenzoates) of formula III,

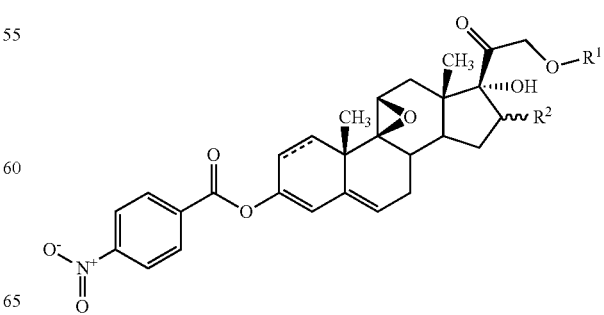

wherein R$^1$ is an acyl group, R$^2$ can be H, alpha methyl or beta methyl, and the dotted line can represent a double bond, are perfectly crystallisable derivatives, obtainable with a purity exceeding 98% and high yields (>90%).

Fluorination (Scheme 2) of the compounds of formula III with electrophilic fluorinating agents such as 1-chloromethyl-4-fluoro-1,4-diazonia-bicyclo[2,2,2]octane bis tetrafluoroborate or 1-fluoro-4-hydroxy-1,4-diazoniabicyclo[2,2,2]octane bis tetrafluoroborate, available under the tradename Selectfluor or Accufluor, in inert solvents and in the presence of basic catalysts, produces the corresponding 6α-fluoro derivatives of formula I having an α/β ratio of 99.5/0.5 and an overall HPLC purity of about 98%. In the compounds of formula I and III, R$^1$ is preferably acetyl.

It is also surprising that both the 3-(2-nitrobenzoate) and 3-(3-nitrobenzoate) analogues of formula III are not easily crystallisable, and therefore do not supply 6α-fluoro derivatives with the quality characteristics described above.

Scheme 2

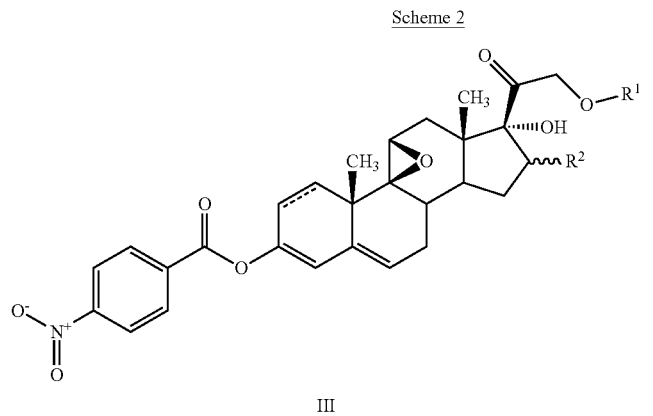

III

Preferably, the inert solvent is acetonitrile and the basic catalyst is pyridine.

The reaction temperature is between 0 and 30° C., preferably ambient temperature.

The compound of formula III is preferably selected from 9β,11-epoxy-16α-methyl-3,17,21-trihydroxy-1,3,5-triene-20-one-21-acetate-3-(4-nitrobenzoate). 9β,11-epoxy-16β-methyl-3,17,21 -trihydroxy-1,3,5-triene-20-one-21-acetate-3-(4-nitrobenzoate) and 9β,11-epoxy-3,17,21-trihydroxy-1,3,5-triene-20-one-21-acetate-3-(4-nitrobenzoate).

The advantages of the process according to the invention are summarised below:
very high α/β selectivity, normally 99.5/0.5.
near absence of co-products or other impurities deriving from the enol esterification reaction in the 3 position.
high chemical yields.
very high HPLC purity: one recrystallisation is sufficient to obtain the pure 6α-fluoro derivative meeting ICH guidelines.
easy industrialisation of the process.

The following examples illustrate the invention.

Example 1

9β,11 -epoxy-16α-methyl-3,17,21-trihydroxy-1,3,5-triene-20-one-21-acetate-3-(4-nitrobenzoate)

A solution of 9β,11-epoxy-16α-methyl-17,21-dihydroxy-1,4-diene-3,20-dione-21-acetate (16.2 g) in 45 mL of pyridine is heated to 75° C. 4-nitrobenzoyl chloride (9.7 g) is added slowly under nitrogen. The reaction mixture is maintained at 75° C. under nitrogen for about 2 hours. The mixture is cooled to ambient temperature and poured slowly into a mixture of ice (160 g), methylene chloride (160 mL) and 30% sulphuric acid (60 mL). After phase separation, the aqueous phase is extracted again with 160 mL of methylene chloride. The combined organic phases are washed 3 times with a dilute solution of sodium bicarbonate and then with water. The organic solution is concentrated to a small volume, methanol (80 mL) is added, and the solution is concentrated again until the methylene chloride has been completely eliminated. The solid that crystallises is filtered and dried under vacuum to give 20 g of title compound with 99.1% purity.

Example 2

9β,11-epoxy-16β-methyl-3,17,21-trihydroxy-1,3,5-triene-20-one-21-acetate-3-(4-nitrobenzoate)

With the same procedure as described in example 1 but using 9β,11-epoxy-16β-methyl-17,21-dihydroxy-1,4-diene-3,20-dione-21-acetate (16.2 g) as raw material, 20.2 g of 98.3% pure title compound is obtained.

Example 3

9β,11-epoxy-3,17,21-trihydroxy-1,3,5-triene-20-one-21 -acetate-3 -(4-nitrobenzoate)

Using the same procedure as in example 1, but starting with 9β,11-epoxy-17,21-dihydroxy-1,4-diene-3,20-dione-21-acetate (36 g), 45.2 g of 98.6% pure title compound is obtained.

Example 4

9β,11-epoxy-6-α-fluoro-16α-methyl-17,21-dihydroxy-1,4-diene-3,20-dione-21-acetate The product of example 1 (16.9 g) is suspended in acetonitrile (130 mL) and pyridine (1,5 mL).

Selectfluor (10.6 g) is added in portions under nitrogen and left to react for about 1 hour, obtaining the solubilisation of the solid. The solution is diluted with 130 mL of water and the organic solvent is eliminated by distillation under vacuum, 150 mL of methylene chloride is added to the residue, and the phases separate. The organic phase is concentrated to a small volume, and 80 mL of methanol is added. Concentration continues until the methylene chloride has been completely eliminated. The solid that crystallises is filtered and dried to give 11 g of title compound with the α/βratio 99.5/0.5. The overall purity is 98.2%.

Example 5

9β,11-epoxy-6-α-fluoro-16β-methyl-17,21-dihydroxy-1,4-diene-3,20-dione-21-acetate With the same procedure as described in example 4, but using 16.9 g of the compound of example 2 as raw material, 10.6 g of the title compound with the α/β ratio 99.6/0.4 is obtained.

The overall purity is 97.9%.

Example 6

9β,11-epoxy-6-α-fluoro-17,21-dihydroxy-1,4-diene-3,20-dione-21-acetate

With the same procedure as described in example 4, but using 38.4 g of the compound of example 3, 23.8 g of the title compound with the α/β ratio 99.4/0.6 is obtained. The overall purity is 97.8%.

The invention claimed is:

1. Process for the preparation of 6-α-fluoro pregnanes of formula I

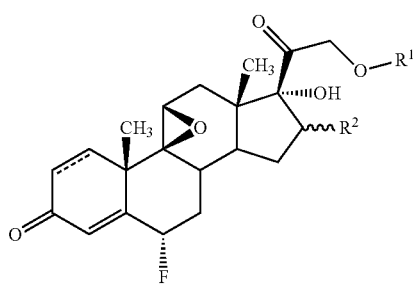

wherein $R^1$ is an acyl group, $R^2$ can be H, alpha methyl or beta methyl and the dotted line can represent a double bond, comprising fluorination with electrophilic fluorinating agents at the 6 position of compounds of formula III,

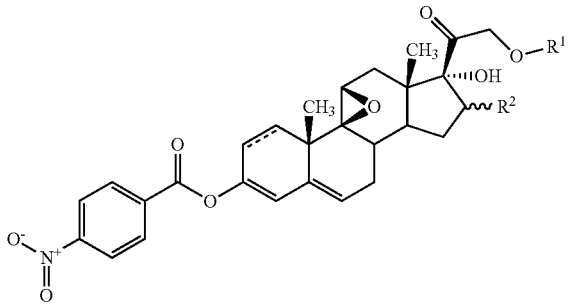

wherein $R^1$, $R^2$ and the dotted line have the meanings given above, in an inert solvent, in the presence of a basic catalyst and at temperatures ranging from 0 to 30° C.

2. A process according to claim 1, wherein the electrophilic fluorinating agent is 1-chloromethyl-4-fluoro-1,4-diazoniabicyclo[2,2,2]octane bis tetrafluoroborate or 1-fluoro-4-hydroxy-1,4-diazoniabicyclo[2,2,2]octane bis tetrafluoroborate.

3. A process according to claim 1, wherein the inert solvent is acetonitrile.

4. A process according to claim 1, wherein the basic catalyst is pyridine.

5. A process according to claim 1, wherein the preferred reaction temperature ranges from 15 to 25° C.

6. A process according to claim 1, wherein R' is acetyl.

7. A process according to claim 1, wherein the compound of formula III is 9β,11-epoxy-16α-methyl-3,17,21-trihydroxy-1,3,5-triene-20-one-21-acetate-3-(4-nitrobenzoate).

8. A process according to claim 1, wherein the compound of formula III is 9β,11-epoxy-16β-methyl-3,17,21-trihydroxy-1,3,5-triene-20-one-21-acetate-3-(4-nitrobenzoate).

9. A process according to claim 1, wherein the compound of formula III is 9β,11-epoxy-3,17,21-trihydroxy-1,3,5-triene-20-one-21-acetate-3-(4-nitrobenzoate).

* * * * *